United States Patent [19]

Jacquess et al.

[11] Patent Number: 5,902,820
[45] Date of Patent: May 11, 1999

[54] MICROBICIDAL COMPOSITIONS AND METHODS USING COMBINATIONS OF PROPICONAZOLE WITH DODECYLAMINE OR A DODECYLAMINE SALT

[75] Inventors: Percy A. Jacquess, Tigrett; David Oppong; Sheldon M. Ellis, both of Cordova; L. Fernando Del Corral, Memphis, all of Tenn.

[73] Assignee: Buckman Laboratories International Inc., Memphis, Tenn.

[21] Appl. No.: 08/821,912

[22] Filed: Mar. 21, 1997

[51] Int. Cl.$^6$ .......................... A01N 33/02; A01N 37/30; A01N 43/36; A01N 43/64

[52] U.S. Cl. .......................... 514/383; 514/554; 514/663; 504/156; 504/158; 504/160

[58] Field of Search .................. 514/383, 554, 514/663; 504/156, 158, 160

[56] References Cited

U.S. PATENT DOCUMENTS 5,322,834  6/1994  Hsu et al. .................. 504/156

FOREIGN PATENT DOCUMENTS

| 0 393 746 A1 | 10/1990 | European Pat. Off. . | |
|---|---|---|---|
| 0 544 418 A2 | 2/1993 | European Pat. Off. . | |
| 646207 | 11/1950 | United Kingdom | 514/663 |
| 1202041 | 8/1970 | United Kingdom | 514/554 |

OTHER PUBLICATIONS

Tomlin, The Pesticide Manual, $10_{th}$ Ed. (1995) pp. 855–857.

*Primary Examiner*—Allen J. Robinson
*Attorney, Agent, or Firm*—Morgan, Lewis & Bockius LLP

[57] ABSTRACT

Microbicidal compositions are described. The compositions contain (a) propiconazole and (b) dodecylamine or a dodecylamine salt. The propiconazole and dodecylamine or dodecylamine salt are present in a synergistically effective amount to control the growth of at least one microorganism. Methods for controlling the growth of microorganisms on various substrates or in aqueous systems are also described. Also described is the industrial application of the microbicidal composition in the leather industry, the lumber industry, the papermaking industry, the textile industry, the agricultural industry, and the coating industry, as well as in aqueous systems.

28 Claims, No Drawings

MICROBICIDAL COMPOSITIONS AND METHODS USING COMBINATIONS OF PROPICONAZOLE WITH DODECYLAMINE OR A DODECYLAMINE SALT

BACKGROUND OF THE INVENTION

1. Field of the Invention

The present invention relates to compositions for controlling the growth of microorganisms on a variety of substrates and in aqueous systems. More particularly, the invention relates to combinations of propiconazole, also known as (RS)-1-2-[(2,4-dichlorophenyl)-2-propyl-1,3-dioxalan-2-ylmethyl]-1H-1,2,4-triazole, with dodecylamine or a dodecylamine salt. The invention also relates to the use of such combinations as microbicides.

2. Background of the Invention

A large variety of commercial, industrial, agricultural, and wood materials or products are subject to microbiological attack or degradation which reduces or destroys their economic value. Examples of such materials or products include surface coatings, lumber, seeds, plants, leather and plastics. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

Aqueous systems are also highly subject to microbiological growth, attack, and degradation. The aqueous system may be a fresh, brackish or saltwater system. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiologic growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Microbiological degradation can have a direct adverse economic impact when it occurs in industrial process waters, for example in cooling waters, metal working fluids, or other recirculating water systems such as those used in papermaking or textile manufacture. If not controlled, microbiological degradation of industrial process waters can interfere with process operations, lower process efficiency, waste energy, plug the water-handling system, and even degrade product quality.

For example, cooling water systems used in power plants, refineries, chemical plants, air-conditioning systems, and other industrial operations frequently encounter microbiological degradation problems. Airborne organisms entrained from cooling towers as well as waterborne organisms from the system's water supply commonly contaminate these aqueous systems. The water in such systems generally provides an excellent growth medium for these organisms. Aerobic and heliotropic organisms flourish in the towers. Other organisms grow in and colonize such areas as the tower sump, pipelines, heat exchangers, etc. If not controlled, the resulting microbiological degradation can plug the towers, block pipelines, and coat heat-transfer surfaces with layers of slime and other biologic mats. This prevents proper operation, reduces cooling efficiency and, perhaps more importantly, increases the costs of the overall process.

Industrial processes subject to microbiological degradation also include papermaking, the manufacture of pulp, paper, paperboard, etc. and textile manufacture, particularly water-laid non-woven textiles. These industrial processes generally recirculate large amounts of water under conditions which favor the growth of microbiological degradation organisms.

Paper machines, for example, handle very large volumes of water in recirculating systems called "white water systems." The furnish to a paper machine typically contains only about 0.5% of fibrous and non-fibrous papermaking solids, which means that for each ton of paper almost 200 tons of water pass through the headbox. Most of this water recirculates in the white water system. White water systems provide excellent growth media for microbiological degradation organisms. That growth can result in the fromation of slime and other deposits in headboxes, waterlines, and papermaking equipment. Such microbiological degradation not only can interfere with water and stock flows, but when loose, can cause spots, holes, and bad odors in the paper as well as web breaks, all of which translate into costly disruptions in paper machine operations.

Slime formation can occur in other aqueous systems including fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Various chemicals known as industrial microbicides have been used to prevent microbiological deterioration or degradation of industrial systems, raw materials, and products. Some of these biocides, however, are of questionable practical utility because they have undesirable odors, are high in cost, show low degree of effectiveness or create hazards with respect to storage, use, or handling. For instance, the use of such popular industrial microbicides as organomercurial compounds, organotin compounds and chlorinated phenols have come under great regulatory pressure in recent times because of their high toxicity and concern about their adverse effects on the environment.

Propiconazole, also known as (RS)-1-2-[(2,4-dichlorophenyl)-2-propyl-1,3-dioxalan-2ylmethyl]1H-1,2, 4-triazole, is one commercial biocide which has been shown to have a reasonably good toxicological profile and biocidal activity. However, at low concentrations, propiconazole may have a relatively narrow antimicrobial spectrum and may not completely prevent the growth of microorganisms.

Despite the existence of current microbicides, workers in the trade have continued to seek improved biocides which possess low toxicity while exhibiting a prolonged biocidal effect at normal use levels. The improved microbicide should also preferably be more economical and cost-effective offering equal or better protection at lower cost and lower concentration. The concentration of conventional microbicides and the corresponding treatment costs for such use, can be relatively high. Thus, important factors in the search for improved microbicides include the duration of microbicidal effect, the ease of use, and the effectiveness of the microbicide per unit weight.

SUMMARY OF THE INVENTION

In view of industry's search for improved microbicides, the present invention offers an improvement over current biocides and practices. A first embodiment of the invention provides a microbicidal composition. This composition comprises propiconazole and dodecylamine or a dodecylamine salt. In the microbicidal composition, the propiconazole and the dodecylamine or dodecylamine salt are present in a synergistically effective amount to control the growth of at least one microorganism. This combination according to the invention achieves superior microbicidal activity at lower concentrations and lower cost than propiconazole alone against microbiological attack or degradation such as discussed above.

Another embodiment of the present invention provides a method for controlling the growth of a microorganism on a substrate. This method comprises contacting the substrate with propiconazole and dodecylamine or a dodecylamine salt. The propiconazole and the dodecylamine or dodecylamine salt are present in a synergistically effective amount to control the growth of at least one microorganism on the substrate.

Another embodiment of the invention provides a method for controlling the growth of microorganisms in an aqueous system capable of supporting growth of a microorganism. This method comprises the step of treating the aqueous system with propiconazole and dodecylamine or dodecylamine salt, where the propiconazole and the dodecylamine or dodecylamine salt are present in a synergistically effective amount to control the growth of at least one microorganism in the aqueous system.

The combination of propiconazole and dodecylamine or a dodecylamine salt is useful in preventing the microbiological attack, degradation, or deterioration of various types of raw materials and products such as leather, textiles, pulp, paper and paperboard, coatings, lumber, as well as agricultural products such as seeds and crops. Advantageously, such a combination may be used in various industrial processes used to prepare or manufacture these products. Accordingly, additional embodiments of the present invention employ the combination to control the growth of microorganisms on or in such industrial products, raw materials or processes.

The features and advantages of the present invention will be made more apparent from the following detailed description and preferred embodiments.

DETAILED DESCRIPTION OF THE INVENTION

As discussed above, the invention relates to combinations of propiconazole, also known as (RS)-1-2-[(2,4-dichlorophenyl)-2-propyl-1,3-dioxalan-2ylmethyl]-1H-1,2, 4-triazole, with dodecylamine or a dodecylamine salt. Mixtures of dodecylamine and its salts may also be used.

The dodecyl group of the dodecylamine or a dodecylamine salt may be branched or unbranched, i.e., straight chain. Preferably, the dodecyl group is unbranched. The dodecyl group may be unsubstituted or substituted by one or more substituents that do not adversely effect the activity of the inventive salts. Illustrative examples of suitable substituents include alkyl groups, alkenyl groups, alkoxy groups, aryl groups, aralkyl groups, hydroxy groups, oxo groups (to form a ketone), acid groups and derivatives thereof, such as esters and amides, and halogen atoms. Preferably, the dodecyl group is unsubstituted.

The salts of dodecylamine employed in the present invention preferably have the following general formula:

$$C_{12}H_{25}NH_3^+Z^-$$

in which Z is an anion or a fraction of a polyvalent counter ion sufficient to balance the cationic charge in the dodecylamine. The anion Z is preferably the conjugate base of an organic acid, i.e., Z is derived from an organic acid by loss of an ionizable proton. Illustrative examples of suitable organic acids are the mono- and di-carboxylic acids.

Preferably, Z is derived from an acyclic, cyclic, or aromatic mono- or dicarboxylic acid. The carboxylic acid preferably has up to ten carbon atoms. If cyclic or aromatic, the ring may contain one or more heteroatoms, such as N, O, or S. The carboxylic acid may also be substituted by any suitable substituent that does not adversely effect the activity of the inventive compositions. Illustrative examples of suitable substituents include alkyl groups, substituted alkyl groups, alkenyl groups, substituted alkenyl groups, amino groups, oxo groups, halogen atoms, etc.

Illustrative examples of useful carboxylic acid groups include: acetyl, propionyl, butyryl, citral, lactyl, valeryl, phthalyl, succinyl, octanoyl, nonanoyl, formyl, sorbyl, oxalyl, lauryl, cyclohexanoyl and benzoyl. One of ordinary skill will recognize that other organic acid groups may also be used in the present invention.

One or more of the hydrogen atoms bound to the nitrogen atom may be replaced by a suitable substituent to give a secondary, tertiary, or quaternary amine salt of dodecylamine. Preferably, a primary amine salt of dodecylamine is employed.

The following carboxylic acid salts of dodecylamine are particularly preferred in the practice of the present invention: dodecylamine acetate, dodecylamine maleate, dodecylamine malonate, dodecylamine propionate, dodecylamine butyrate, dodecylamine citrate, dodecylamine lactate, dodecylamine valerate, dodecylamine phthalate, dodecylamine succinate, dodecylamine hydroxysuccinate, dodecylamine octanoate, dodecylamine nonanate, dodecylamine formate, dodecylamine sorbate, dodecylamine oxalate, dodecylamine laurate, dodecylamine cyclohexanoate, dodecylamine benzoate, dodecylamine 2-hydroxybenzoate, dodecylamine 3-hydroxybenzoate, or dodecylamine 4-hydroxybenzoate. More particularly preferred of these compounds are dodecylamine acetate, dodecylamine propionate, and dodecylamine benzoate.

The salts of dodecylamine are preferably prepared by reacting dodecylamine with the desired acid in the presence of a suitable solvent. Suitable acids groups are available in their acid or salt form either commercially from laboratory supply houses or can be prepared from readily available starting materials using well-known literature methods. The synthesis of the amine salts generally can be carried out in a solvent which may be a solvent for at least one of the reactants but which is generally a solvent for the desired product. Preferred solvent systems include inorganic acids and organic acids or alcohols. Most preferred is acetic acid.

The reaction temperature may be readily determined by one skilled in the art depending on the particular reactants employed. Preferably the temperature of reaction varies from 40° C. to 110° C. or more, more preferably the temperature of the reaction is between 70° C. and 100° C. The reaction is allowed to proceed until complete, as shown, for example, by a pH meter (the reaction is complete when the pH meter indicates that the limiting reactant has been neutralized). Generally, the reaction is stirred for 30 min to 2 hours, preferably for about 1 to 2 hours.

After the reaction is complete, the reaction product can be worked up using well-known techniques to isolate and purify the desired salt of dodecylamine. Excess reactants and any solids formed during the reaction can be filtered off, and the filtrate evaporated to yield the crude product. In cases where the desired salt compound is a solid, the product of the reaction may be recrystallized from an appropriate solvent to yield a more pure compound. It should be noted, however, that both pure and crude salts of dodecylamine can be used for in the compositions and methods of this invention. The preparation of the dodecylamine salts is not limited to the exact process or steps described above. Any of procedures known to the art which yield the desired end product may be used.

In one embodiment, the present invention relates to a microbicidal composition comprising propiconazole and dodecylamine or a dodecylamine salt. The propiconazole and the dodecylamine or dodecylamine salt are present in a synergistically effective amount to control the growth of at least one microorganism.

Depending on the application, microbicidal compositions according to the present invention may be prepared in various forms known in the art. For example, the composition may be prepared in liquid form as an aqueous solution, dispersion, emulsion, or suspension, a dispersion or suspension in a non-solvent, or as a solution by dissolving the propiconazole and the dodecylamine or dodecylamine salt in a solvent or combination of solvents. Suitable solvents include, but are not limited to, methyl ethers of glycols, M-pyrol or petroleum distillates. The microbicidal composition may be prepared as a concentrate for dilution prior to its intended use. Common additives such as surfactants, emulsifiers, dispersants, and the like may be used as known in the art to increase the solubility of the propiconazole, dodecylamine, or dodecylamine salt in a liquid composition or system, such as an aqueous composition or system. In many cases, the biocidal composition of the invention may be solubilized by simple agitation.

Microbicidal compositions of the present invention may also be prepared in solid form, for example as a powder or tablet, using means known in the art. In a preferred method of preparation, a liquid product containing propiconazole is deposited on a carrier such as diatomaceous earth zeolites, kaolin, or a water-soluable matrix and mixed with the dodecylamine or dodecylamine salt in the form of a liquid or solution to form a powder or tablet.

The propiconazole and the dodecylamine or its salt may be combined in a single composition. Alternatively, the propiconazole and the dodecylamine or dodecylamine salt may be employed as separate components such that combined amount for the intended use is synergistically effective to control the growth of at least one microorganism.

As mentioned above, a microbicidal composition of the invention demonstrates an unexpected enhanced microbicidal effect between the respective components, propiconazole and dodecylamine or a dodecylamine salt. That is, the combination according to the invention achieves superior microbicidal activity at lower concentrations to control the growth of microorganisms as compared to the microbicidal capability of either component alone. Thus, the combination synergistically enhances the microbicidal effect of the individual components. Such a superior effect presents a distinct economic advantage and increases the microbicide's effectiveness per unit weight.

According to the present invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The combination of propiconazole with dodecylamine or a dodecylamine salt as described here can, in many cases, reduce the total microbiological count to undetectable limits and maintain the count at that level for a significant period of time. Accordingly, the combination may be used to preserve a substrate or system.

The effective amount or percentage of the combination of propiconazole and dodecylamine or its salt acid necessary to achieve the desired result may vary somewhat depending on the substrate or aqueous system to be protected, the conditions for microbial growth, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 0.2%. With aqueous systems, an effective amount may range from about 0.5 to about 5000 parts per million, more preferably from about 5 to about 1000 parts per million of the aqueous system, and most preferably from, about 10 to about 25 parts per million. Similar amounts effectively control slime formation. For slime control, effective amounts preferably range from about 1 to about 200 parts per million, and more preferably, from about 1 to about 25 parts per million of the aqueous system.

In a preferred embodiment, combinations of propiconazole and dodecylamine or a dodecylamine are those combinations having a weight ratio from about 99:1 to about 1:99. More preferably the weight ratio is from about 60:10 to about 10:60, and most preferably, from about 50:50 to about 25:75. The weight ratio may vary depending on the intended use, the microorganism encountered as well as the particular material, product, or system to which the combination according to the invention is applied.

A combination of propiconazole with dodecylamine or a dodecylamine salt may be applied in a variety of industrial uses and processes for microorganism control. The combination of the invention may be used in place of and in the same manner as other microbicides traditionally used in the particular industry. As discussed above, such industries include, but are not limited to the leather industry, the lumber industry, the papermaking industry, the textile industry, the agricultural industry, and the coating industry. Combinations of propiconazole and dodecylamine or a dodecylamine salt may also be used with aqueous systems such as those previously discussed which are subject to microbiological attack and degradation. The problems caused by microbiological attack and deterioration in these various applications has been described above. The use of a combination according to the invention to control the growth of microorganisms in particular exemplary applications is described below.

The invention also relates to a method for controlling the growth of microorganisms on various substrates. The method comprises the step of contacting a substrate susceptible to microbiological growth or attack with propiconazole and dodecylamine or a dodecylamine salt, as described above. The propiconazole and the dodecylamine or dodecylamine salt are present in a synergistically effective amount to control the growth of at least one microorganism on the substrate. Preferably, the method may be used to eliminate or prevent substantially all microbiological growth on the substrate. As discussed above, the components of a combination according to the invention may be applied together or as separate compositions. Preferred applications of this general method are discussed below.

In the leather industry, a combination of propiconazole and dodecylamine or a dodecylamine salt may be used to control the growth of microorganisms on a hide during a tanning process. To achieve this control, the hide is contacted with a combined amount of propiconazole and dodecylamine or a dodecylamine salt synergistically effective to control the growth of at least one microorganism on the hide. The combination of the invention may be used in the tanning process in similar amounts and manner similar to that used to apply other microbicides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retanning stage, a dyeing stage, and a fatliquoring stage. The combination of propiconazole and dodecylamine or a dodecylamine salt may be used during all process stages in the tanning process in addition to those stages where a known microbiological problem is occurring. In each stage, the combination may be a component of the appropriate tanning liquor applied to the hide undergoing tanning.

Incorporating the propiconazole and dodecylamine or a dodecylamine salt in a tanning liquor protects the hide from microbiological deterioration during the tanning process. Preferably, the combination is uniformly dispersed, e.g., under agitation, into an appropriate liquor to be used in a tanning process. Typical tanning liquors include, for example, a pickling liquor, a chrome-tanning liquor, a vegetable-tanning liquor, a post-tan washing liquor, a retanning liquor, a dye liquor, and a fatliquor. This method of application ensures that the combination applied to the hides protects against microbiological attack, deterioration, or other microbiological degradation.

In a somewhat analogous nature, the combination of the invention may also be employed to control the growth of microorganisms on a textile substrate in a textile manufacturing process. Contacting the textile substrate with a synergistic combination of propiconazole and dodecylamine or a dodecylamine salt according to the invention effectively controls the growth of a microorganism on the textile substrate. In a textile process, the combination may be used in similar amounts and a manner similar to other microbicides commonly used in such processes. As one of ordinary skill would appreciate, particular amounts generally depend on the textile substrate and the degree of microbiological resistance required.

The step of contacting the textile substrate with the combination of propiconazole and dodecylamine or a dodecylamine salt may be accomplished using means known in the textile art. To control microbiological growth, a textile process generally dips the textile substrate into a bath containing a microbicide, alone or with other chemicals used to treat the textile substrate. Alternatively, the textile substrate may be sprayed with a formulation containing a microbicide. In the bath or the spray, the propiconazole and dodecylamine or dodecylamine salt are present in a synergistically effective amount to control the growth of at least one microorganism on the textile substrate. Preferably, the bath and the spray are aqueous-based compositions.

To preserve the value of its raw materials and products, the lumber industry also must control the growth of microorganisms in order to prevent microbiological degradation. A combination of propiconazole and dodecylamine or a dodecylamine salt according to the invention is effective to control the growth of microorganisms on lumber.

A combination of propiconazole with dodecylamine or a dodecylamine salt may be used to protect the lumber in similar amounts and a similar manner employed for other microbicides used in the lumber industry. Contacting lumber with an effective amount of the combination may be accomplished, for example, by spraying the lumber with an aqueous formulation containing the combination, by dipping the lumber into a dip bath containing the combination, or other means known in the art. Dipping the lumber in an aqueous bath is preferred.

The propiconazole and dodecylamine or dodecylamine salt are preferably uniformly dispersed in a bath (for example, by agitation) prior to the dipping of the lumber into the bath. In general, the lumber is dipped into the bath, raised, allowed to drip dry, and then air dried. The dip time will depend, as is known in the art, on a variety of factors such as the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath containing the microbicidal combination.

The combination of propiconazole and dodecylamine or dodecylamine salt according to the invention also has uses in the agricultural industry. To control the growth of microorganisms on a seed or plant, the seed or plant may be contacted with propiconazole and dodecylamine or a dodecylamine salt in a synergistically effective amount to control the growth of at least one microorganism on the seed or plant. This contacting step may be accomplished using means and amounts known in the agricultural industry for other microbicides. For example, the seed or plant may be sprayed with an aqueous formulation containing a combination of the invention or dipped into a bath containing the combination. After being sprayed or dipped, the seed or plant is generally dried by means known in the art such as drip drying, heated drying, or air drying. For plants or crops, the combination may also be applied using a soil drench. A soil drench is particularly advantageous when the microorganisms of concern inhabit the soil surrounding the plant.

Yet another aspect of the present invention is a method for controlling the growth of microorganisms in an aqueous system capable of supporting such growth. The aqueous system is treated with propiconazole and dodecylamine or a dodecylamine salt such that the combination is present in an amount synergistically effective to control the growth of at least one microorganism in the aqueous system. This includes controlling, and preferably preventing, slime formation in the aqueous system.

Examples of various aqueous systems include, but are not limited to, latexes, surfactants, dispersants, stabilizers, thickeners, adhesives, starches, waxes, proteins, emulsifying agents, cellulose products, aqueous emulsions, aqueous detergents, coating compositions, paint compositions, alum compositions, and resins formulated in aqueous solutions, emulsions or suspensions. The combination may also be employed in aqueous systems used in industrial processes such as metal working fluids, cooling waters (intake cooling water, effluent cooling water, and recirculating cooling water), waste waters including waste waters or sanitation waters undergoing treatment of the waste in the water, e.g. sewage treatment, and other recirculating water systems such as those used in papermaking or textile manufacture.

As with the other uses discussed above, the combination of the invention may be used in the same amounts and in the same manner as microbicides traditionally used in these various aqueous systems. The combination may not only protect the aqueous system prior to use or when stored, but in many cases protects the aqueous system when in use or in appropriate applications even after the aqueous system has dried. When used in a paint formulation for example, the combination not only protects the paint in the can, but also the paint film after being applied to a substrate.

Another embodiment of the present invention is a method for controlling the growth of microorganisms on paper or in a papermaking process, e.g., in a pulp or paper slurry and on a finished paper product such as paper board. The paper, pulp, or slurry is contacted with propiconazole and dodecylamine or a dodecylamine salt in a synergistically effective amount to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with a combination according to the invention by spraying an aqueous dispersion containing the combination onto the pulp after the pulp leaves the presses in a papermaking process. Or, a combination of propiconazole with dodecylamine or a dodecylamine salt may be incorporated into a bath used at the wet or size press and the web contacted by nipping the web to incorporate the combination into the web with any other agents applied at the press. Alternatively, the pulp may be contacted by mixing propiconazole with dodecylamine or a dodecylamine salt into the pulp/white water mixture, preferably prior to the pulp reaching the formation wire.

When treating paper (which includes paperboard and other cellulosic products or substrates), the propiconazole and dodecylamine or dodecylamine salt may be added into pulp slurries in the headbox, in the substrate forming solution, or in the white water system to treat the water system itself or for incorporation into the body of the paper. Alternatively, as with other known microbicides, a combination of the invention may be mixed into a coating used to coat the finished paper.

As discussed above, the mode as well as the rates of application of the composition of this invention could vary depending upon the intended use. The composition could be applied by spraying or brushing onto the material or product. The material or product in question could be also treated by dipping in a suitable formulation of the composition. In a liquid or liquid-like medium, the composition could be added into the medium by pouring, or by metering with a suitable device so that a solution or a dispersion of the composition could be produced.

The synergistic activity of combinations of propiconazole and dodecylamine or a salt of dodecylamine according to the invention has been confirmed using standard laboratory techniques as illustrated below. The following examples are intended to illustrate, not limit, the present invention.

EXAMPLES

When two chemical microbicides are combined into one product or added separately three results are possible:

1) The resulting product would produce an additive (neutral) effect.
2) The products in the product would produce an antagonistic effect, or
3) The chemicals in the product would produce a synergistic effect.

An additive effect has no economic advantage over the individual components. The antagonistic effect would produce a negative impact. Only synergism, which is less likely than either an additive or antagonistic effect, would produce a positive effect and therefore be of economic advantage.

It is well-known in the microbicidal literature that there is no theoretical method to provide the likelihood of knowing, before actually testing, whether additive, antagonistic or synergistic effects will be obtained when two biocides are mixed to yield a formulation.

A microbicidal composition combining propiconazole and either dodecylamine or its carboxylic acid salt such as dodecylamine propionate, dodecylamine benzoate, or dodecylamine acetate can demonstrate an unexpected synergistic effect compared to the respective components alone and thus achieve superior, i.e. greater than additive microbicidal activity at low concentrations against a wide variety of microorganisms.

Fungal evaluation

Mineral salts-glucose medium was used. To prepare the medium, the following ingredients were added to 1 liter of deionized water: 0.7 g of $KH_2PO_4$, 0.7 g of $MgSO_4.7H_2O$, 1.0 g of $NH_4NO_3$, 0.005 g NaCL, 0.002 g $FeSO_4.7H_2O$, 0.002 g $ZnSO_4.7H_2O$, 0.001 g $MnSO_4.7H_2O$, 10 g of Glucose. The pH of the medium was adjusted to 6 with 1N NaOH. The medium was distributed in 5 mL amounts in test tubes and autoclaved at 121° C. for 20 minutes. The fungi, *Trichoderma harzianum* and *Trichoderma viride* were grown on a potato dextrose agar slant for 7 to 10 days and a spore suspension prepared by washing down the spores from the slant into a sterile saline solution. After addition of the biocides in the desired concentrations to the sterile mineral salts-glucose medium, the fungal spore suspension was added. The final spore concentration was approximately $10^6$ cfu/mL. The inoculated media was incubated at 28° C. for 14 days.

In the Examples 1 through 3, synergism was demonstrated in separate experiments by testing combinations of propiconazole (component A) and dodecylamine or a corresponding salt (component B) in a series of tests in varying ratios and a range of concentrations against the fungi *Trichoderma harzianum* and *Trichoderma viride* using the methods described above. The lowest concentration of each mixture or compound which completely prevented growth of the fungi for two weeks was taken as the end points for synergism calculations. End points for the various mixtures were then compared with the end points for the pure active ingredients alone in concomitantly prepared flasks or test tubes.

Synergism was demonstrated by the method described by Kull, E. C., Eisman, P. C., Sylwestrwicz, H. D., and Mayer, R. L. 1961, Applied Microbiology, 9: 538–541 using the sum:

QA/Qa+QB/Qb where

Qa=Concentration of compound A in parts per million, acting alone, which produced an end point.

Qb=Concentration of compound B in parts per million, acting alone, which produced an end point.

QA=Concentration of compound A in parts per million, in the mixture, which produced an end point.

QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the Kull, et al. Further information concerning this procedure is contained in U.S. Pat. No. 3,231,509.

The Examples demonstrate that combinations of propiconazole with dodecylamine or one of its carboxylic acid salt such as dodecylamine propionate, dodecylamine benzoate or dodecylamine acetate produced a synergistic result indicated by a ratio value of less than one. There were a few samples, such as Table 1, 1.25 or <1.5, where synergistic results were inconclusive because endpoints for propiconazole used alone were not determined. In general, however, an effective fungicidal and bactericidal?? response can be obtained when the synergistic combination is employed in concentrations ranging from about 0.01 to 5000 ppm of propiconazole, preferably 0.1 to 3000 ppm, and most preferably 0.1 ppm to 1000 ppm, and from about 0.1 to about 1% of dodecylamine or its carboxylic acid salt such as dodecylamine propionate, dodecylamine benzoate or dodecylamine acetate preferably 0.1 to 5000 ppm, and most preferably 0.1 to 2000 ppm.

Example 1

Component A = Propiconazole, Component B = Dodecylamine propionate

Quantities producing end points (ppm)

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | >250 | — | — | — | — | — | — |
| | — | 62.5 | — | 25 | 0.25 | 0.25 | 0.5 |
| | — | 125 | — | 25 | 0.5 | 0.25 | 0.75 |
| | — | 250 | — | 25 | 1 | 0.25 | 1.25 |
| | — | 12.5 | — | 50 | 0.05 | 0.5 | 0.55 |
| | — | 25 | — | 50 | 0.1 | 0.5 | 0.6 |
| | — | 62.5 | — | 50 | 0.25 | 0.5 | 0.75 |
| | — | 125 | — | 50 | 0.5 | 0.5 | <1 |
| | — | 250 | — | 50 | 1 | 0.5 | 1.5 |
| | — | — | 100 | — | — | — | — |
| Trichoderma harzianum | >250 | — | — | — | — | — | — |
| | — | 62.5 | — | 25 | 0.25 | 0.5 | 0.75 |
| | — | 125 | — | 25 | 0.5 | 0.5 | <1 |
| | — | 250 | — | 25 | 1 | 0.5 | 1.5 |
| | — | — | 50 | — | — | — | — |

Example 2

Component A = Propiconazole; Component B = Dodecylamine benzoate

Quantities producing end points (ppm)

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | >250 | — | — | — | — | — | — |
| | — | 125 | — | 25 | 0.5 | 0.1 | 0.6 |
| | — | 250 | — | 25 | 1 | 0.1 | 1.1 |
| | — | 62.5 | — | 50 | 0.25 | 0.2 | 0.25 |
| | — | 125 | — | 50 | 0.5 | 0.2 | 0.7 |
| | — | 250 | — | 50 | 1 | 0.2 | 1.2 |
| | — | 62.5 | — | 100 | 0.25 | 0.4 | 0.65 |
| | — | 125 | — | 100 | 0.5 | 0.4 | 0.9 |
| | — | 250 | — | 100 | 1 | 0.4 | 1.4 |
| | — | — | 250 | — | — | — | — |
| Trichoderma harzianun | >250 | — | — | — | — | — | — |
| | — | 125 | — | 25 | 0.5 | 0.25 | 0.75 |
| | — | 250 | — | 25 | 1 | 0.25 | 1.25 |
| | — | 125 | — | 50 | 0.5 | 0.5 | <1 |
| | — | 250 | — | 50 | 1 | 0.5 | 1.5 |
| | — | — | 100 | — | — | — | — |

Example 3

Component A = Propiconazole; Component B = Dodecylamine

Quantities producing end points (ppm)

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 250 | — | — | — | — | — | — |
| | — | 62.5 | — | 5 | 0.25 | 0.1 | 0.35 |
| | — | 125 | — | 5 | 0.5 | 0.1 | 0.6 |
| | — | 62.5 | — | 10 | 0.25 | 0.2 | 0.45 |
| | — | 125 | — | 10 | 0.5 | 0.2 | 0.7 |
| | — | 6.25 | — | 25 | 0.03 | 0.1 | 0.13 |
| | — | 12.5 | — | 25 | 0.05 | 0.5 | 0.55 |
| | — | 25 | — | 25 | 0.1 | 0.5 | 0.6 |
| | — | 62.5 | — | 25 | 0.25 | 0.5 | 0.75 |
| | — | 125 | — | 25 | 0.5 | 0.5 | 1 |
| | — | — | 50 | — | — | — | — |

Example 4

Component A = Propiconazole; Component B = Dodecylamine acetate

Quantities producing end points (ppm)

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 250 | — | — | — | — | — | — |
| | — | 12.5 | — | 25 | 0.05 | 0.25 | 0.3 |
| | — | 25 | — | 25 | 0.1 | 0.25 | 0.35 |
| | — | 62.5 | — | 25 | 0.25 | 0.25 | 0.5 |
| | — | 125 | — | 25 | 0.5 | 0.25 | 0.75 |
| | — | 250 | — | 25 | 1 | 0.25 | 1.25 |
| | — | 0.63 | — | 50 | 0 | 0.5 | 0.5 |
| | — | 1.25 | — | 50 | 0.01 | 0.5 | 0.51 |
| | — | 2.5 | — | 50 | 0.01 | 0.5 | 0.51 |
| | — | 6.25 | — | 50 | 0.03 | 0.5 | 0.53 |
| | — | 12.5 | — | 50 | 0.05 | 0.5 | 0.55 |
| | — | 25 | — | 50 | 0.1 | 0.5 | 0.6 |
| | — | 62.5 | — | 50 | 0.25 | 0.5 | 0.75 |

-continued

Component A = Propiconazole; Component B = Dodecylamine acetate

| Test organism | Quantities producing end points (ppm) | | | | | | |
|---|---|---|---|---|---|---|---|
| | $Q_a$ | $Q_A$ | $Q_b$ | $Q_B$ | $Q_A/Q_a$ | $Q_B/Q_b$ | $Q_A/Q_a + Q_B/Q_b$ |
| | | 125 | | 50 | 0.5 | 0.5 | 1 |
| | | 250 | | 50 | 1 | 0.5 | 1.5 |
| | | | 100 | | | | |

The claimed invention is:

1. A microbicidal composition comprising:
  (a) propiconazole and (b) dodecylamine or a dodecylamine salt, wherein (a) and (b) are present in a synergistically effective amount to control the growth of at least one microorganism.

2. A microbicidal composition according to claim 1, wherein the doedecylamine or dodecylamine salt is at least one selected from the group consisting of: dodecylamine acetate, dodecylamine maleate, dodecylamine malonate, dodecylamine propionate, dodecylamine butyrate, dodecylamine citrate, dodecylamine lactate, dodecylamine valerate, dodecylamine phthalate, dodecylamine succinate, dodecylamine hydroxysuccinate, dodecylamine octanoate, dodecylamine nonanate, dodecylamine formate, dodecylamine sorbate, dodecylamine oxalate, dodecylamine laurate, dodecylamine cyclohexanoate, dodecylamine benzoate, dodecylamine 2-hydroxybenzoate, dodecylamine 3-hydroxybenzoate, and dodecylamine 4-hydroxybenzoate.

3. A microbicidal composition according to claim 1, comprising (a) propiconazole and (b) dodecylamine propionate.

4. A microbicidal composition according to claim 1, comprising (a) propiconazole and (b) dodecylamine benzoate.

5. A microbicidal composition according to claim 1, comprising (a) propiconazole and (b) dodecylamine acetate.

6. A microbicidal composition according to claim 1, comprising (a) propiconazole and (b) dodecylamine.

7. A microbicidal composition according to claim 1, wherein (a) and (b) are present in a combined amount synergistically effective to control the growth of at least one microorganism selected from algae, fungi, and bacteria.

8. A microbicidal composition according to claim 1, wherein the composition is an aqueous formulation.

9. A method for controlling the growth of microorganisms on a substrate comprising the step of contacting a substrate susceptible to the growth of microorganisms with (a) propiconazole and (b) dodecylamine or a dodecylamine salt, wherein (a) and (b) are present in a synergistically effective amount to control the growth of at least one microorganism on the substrate.

10. A method according to claim 9, comprising (a) propiconazole and (b) dodecylamine propionate, dodecylamine benzoate, dodecylamine acetate, or dodecylamine.

11. A method according to claim 9, wherein (a) and (b) are present in a combined amount synergistically effective to control the growth of at least one microorganism selected from algae, fungi, and bacteria.

12. A method for controlling the growth of microorganisms on a hide during a leather tanning process comprising the step of contacting the leather with (a) propiconazole and (b) dodecylamine or a dodecylamine salt, wherein (a) and (b) are present in a synergistically effective amount to control the growth of at least one microorganism on the hide.

13. A liquor for use in a leather-tanning process comprising (a) propiconazole and (b) dodecylamine or a dodecylamine salt, wherein (a) and (b) are present in the liquor in a synergistically effective amount to control the growth of at least one microorganism on the leather.

14. A liquor according to claim 13, wherein the liquor is selected from a pickling liquor, a chrome-tanning liquor, a vegetable-tanning liquor, a post-tan washing liquor, a retanning liquor, a dye liquor, and a fatliquor; and wherein the microorganism is algae, fungi, or bacteria.

15. A method for controlling the growth of microorganisms on a textile substrate in a textile manufacturing process comprising the step of contacting the textile substrate with (a) propiconazole and (b) dodecylamine or a dodecylamine salt, wherein (a) and (b) are present in a synergistically effective amount to control the growth of at least one microorganism on the textile substrate.

16. A method for controlling the growth of microorganisms on lumber comprising the step of contacting the lumber with (a) propiconazole and (b) dodecylamine or a dodecylamine salt, wherein (a) and (b) are present in a synergistically effective amount to control the growth of at least one microorganism on the lumber.

17. A method according to claim 16, wherein the contacting step comprises dipping the lumber in a bath containing (a) and (b).

18. A method according to claim 16, wherein the contacting step comprises spraying an aqueous formulation of (a) and (b) onto the lumber.

19. A method for controlling the growth of microorganisms on a seed or plant comprising the step of contacting the seed or plant with (a) propiconazole and (b) dodecylamine or a dodecylamine salt, wherein (a) and (b) are present in a synergistically effective amount to control the growth of at least one microorganism.

20. A method according to claim 19, wherein the contacting step comprises drenching the soil surrounding a seed or plant with an aqueous formulation of (a) and (b).

21. A method according to claim 19, wherein the contacting step comprises spraying an aqueous formulation of (a) and (b) onto the seed or plant.

22. A method for controlling the growth of microorganisms in an aqueous system capable of supporting growth of a microorganism comprising the step of treating the aqueous system with (a) propiconazole and (b) dodecylamine or a dodecylamine salt, wherein (a) and (b) are present in a synergistically effective amount to control the growth of at least one microorganism.

23. A method according to claim 22, wherein said aqueous system is selected from the group consisting of a latex, a metal working fluid, an aqueous emulsion, an aqueous detergent, a cooling water, a papermaking recirculating water system, a textile manufacturing recirculating water system, white water systems and an aqueous resin formulation.

24. A method for controlling the growth of microorganisms on pulp or paper in a papermaking process, comprising the step of contacting the pulp or paper with (a) propiconazole and (b) dodecylamine or a dodecylamine salt, wherein (a) and (b) are present in a synergistically effective amount to control the growth of at least one microorganism.

25. A method according to claim 24, wherein wet-lap pulp is contacted by spraying an aqueous formulation of (a) and (b) onto the pulp after the pulp leaves a press in the papermaking process.

26. A method according to claim 24, wherein wet-lap pulp is contacted by mixing (a) and (b) into a pulp/white water mixture prior to reaching a formulation wire in a papermaking process.

27. A method according to claim 24, wherein (a) and (b) are incorporated into the body of the paper.

28. A method according to claim 24, wherein contacting step is accomplished by mixing (a) and (b) into a coating composition and applying the coating composition to the finished paper.

* * * * *